United States Patent [19]

Nowack et al.

[11] 4,327,234

[45] Apr. 27, 1982

[54] HYDROGENATION PROCESS USING SUPPORTED NICKEL CATALYST

[75] Inventors: Gerhard P. Nowack; Marvin M. Johnson, both of Bartlesville, Okla.

[73] Assignee: Phillips Petroleum Company, Bartlesville, Okla.

[21] Appl. No.: 213,424

[22] Filed: Dec. 5, 1980

[51] Int. Cl.³ .............................................. C08L 7/00
[52] U.S. Cl. .................... 585/267; 585/266; 585/270; 585/276
[58] Field of Search ............... 585/266, 267, 270, 276

[56] References Cited

U.S. PATENT DOCUMENTS

| | | | |
|---|---|---|---|
| 3,298,966 | 1/1967 | Bagnetto | 252/437 |
| 3,505,421 | 4/1970 | Lumbroso et al. | 585/266 |
| 3,591,618 | 7/1971 | Hanschke | 260/464 |
| 3,595,808 | 7/1971 | Bertsch et al. | 252/437 |
| 4,017,424 | 4/1977 | Johnson et al. | 252/437 |
| 4,071,331 | 1/1978 | Johnson et al. | 48/197 R |
| 4,140,493 | 2/1979 | Johnson et al. | 48/214 A |

*Primary Examiner*—John F. Niebling

[57] ABSTRACT

Unsaturated hydrocarbons are hydrogenated using a catalyst comprising nickel on a calcium phosphate support. The catalyst can be used in combination with a promoter selected from at least one of barium and uranium. Aromatic compounds such as benzene can be hydrogenated in this process. The catalytic activity of the described catalyst is sufficiently great as to permit hydrogenation under relatively mild conditions, including liquid phase hydrogenation of aromatics, thus prolonging the active life of the catalyst.

12 Claims, No Drawings

HYDROGENATION PROCESS USING SUPPORTED NICKEL CATALYST

This invention relates to the catalytic hydrogenation of unsaturated hydrocarbons.

It is known that alumina-supported nickel catalysts are active in promoting the hydrogenation of unsaturated hydrocarbons including aromatic compounds. For example, a conventional hydrogenation process involves the conversion of benzene to cyclohexane in the presence of a nickel-alumina hydrogenation catalyst. The reaction is carried out in mixed liquid-gas phase in a trickle-bed reactor. As the activity of the catalyst declines with use, the reaction temperature is raised to maintain satisfactory conversion. The upper limit for the reactor temperature is about 260° C., because at this temperature ring opening of the cyclohexane becomes excessive. Operation at this final temperature is essentially vapor phase.

It would be desirable to have catalysts which are sufficiently active to carry out such hydrogenation processes in the liquid phase, as liquid-phase operation permits better temperature control of the exothermic hydrogenation reaction and reduces the conditions which lead to coking and sintering of the catalyst, thereby increasing its active life.

It is an object of the invention to provide a process for the hydrogenation of unsaturated hydrocarbons.

It is a further object of the invention to provide an aromatic hydrogenation process which is effective under the conditions of liquid-phase operation.

SUMMARY OF THE INVENTION

According to the invention, unsaturated hydrocarbons are reacted with hydrogen in the presence of a catalyst comprising nickel on a calcium phosphate support. A promoter selected from at least one of barium and uranium can be used with the supported nickel catalyst. The hydrogenation reaction can, if desired, be carried out in the liquid phase under relatively mild hydrogenation conditions.

DETAILED DESCRIPTION OF THE INVENTION

The process of the invention is suitable for the hydrogenation of unsaturated hydrocarbons, including acyclic, alicyclic and aromatic hydrocarbons. As used herein, the term "hydrocarbon" includes compounds containing only hydrogen and carbon and substituents which do not adversely affect the hydrogenation of the carbon-carbon unsaturation. The aromatic hydrocarbons may be monocyclic or polycyclic. They may be substituted or unsubstituted. Examples of suitable aromatic compounds include benzene, toluene, xylenes, ethylbenzene, isopropylbenzene, n-butylbenzene, naphthalene, anthracene and diphenyl. Because of the present commercial importance of the product, the currently preferred feed to the hydrogenation reaction is benzene, which is hydrogenated to cyclohexane.

Olefinic hydrocarbons can also be hydrogenated in the invention process. Examples of suitable compounds containing olefinic unsaturation include propylene, isobutene, n-butenes, cyclohexene, butadiene and isoprene.

The catalyst used in the invention hydrogenation process is a nickel catalyst on a calcium phosphate support optionally used with a promoter selected from barium, uranium and combinations of these. The Ca:P atomic ratio in the support material is within the range of about 1.4:1 to about 2.3:1. The amount of calcium in the catalyst is generally within the range of about 5 to about 35 weight percent, based on the weight of the total catalyst, preferably about 10 to about 25 weight percent. Phosphorus is present generally in the range of about 2 to about 20 weight percent, preferably about 5 to about 15 weight percent. The amount of nickel in the hydrogenation catalyst is generally in the range of about 10 to about 50, preferably about 20 to about 40 weight percent. The amount of barium promoter, if present, can vary from about 1 to about 20 weight percent, preferably about 2.5 to about 18 weight percent. Uranium can be present in the catalyst in an amount within the range of about 2 to about 40, preferably about 10 to about 30 weight percent, based on the total weight of the catalyst. The remainder of the catalyst is combined oxygen.

A presently-preferred support material for the catalyst has a Ca:P atomic ratio within the range of 1.5:1 to 1.8:1. A Ca:P atomic ratio of 1.67 corresponds to calcium hydroxyapatite, $Ca_5(OH)(PO_4)_3$, which is the presently preferred calcium phosphate for the support.

The catalyst compositions used in the invention process are prepared by first preparing the calcium phosphate support. An aqueous solution of a soluble calcium compound is admixed with a soluble phosphate compound to form a calcium phosphate gel having a Ca:P atomic ratio in the range of about 1.4:1 to 2.3:1.

Suitable calcium compounds for preparing the hydrogenation catalyst support include calcium acetate, calcium formate, calcium isobutyrate, and calcium nitrate. The calcium salt is preferably one in which the anion portion is decomposed at calcination temperatures to a gas, leaving no unwanted residue. Suitable phosphate compounds for preparing the hydrogenation catalyst support include ammonium and alkali metal phosphates such as monohydrogen ammonium orthophosphate, sodium orthophosphate, monohydrogen sodium orthophosphate, dihydrogen sodium orthophosphate, potassium orthophosphate, monohydrogen potassium orthophosphate, dihydrogen potassium orthophosphate and potassium pyrophosphate.

It is preferred that substantially all of the phosphorus be combined with the calcium, with no effective amount of the phosphorus being available for combination with the nickel or the promoter metals.

The calcium phosphate gel can be combined with barium, uranium or combinations of these. In a suitable preparation process, the gel is filtered, washed, and reslurried in distilled water. About one-half the desired amount of promoter metal in aqueous solution of a soluble promoter compound is added to the slurried gel. The mixture is allowed to stand for a period of time sufficient to ensure substantial uptake of the promoter metal into the wet gel. The standing period varies with the promoter compound used and the dilution of the gel and promoter solution, but it will generally range from about 4 hours to 4 days, with occasional stirring. To this mixture is added, with stirring, an aqueous solution containing a mixture of the remaining portion of the promoter compound and a soluble nickel compound, together with an alkaline solution of, for example, ammonium hydroxide, an alkali metal hydroxide or an alkali metal carbonate. The alkaline solution is added at a rate such that the pH of the mixture is at least 7, preferably about 7 to 9. The resulting mixture is then filtered, washed, refiltered and dried in air at about 105° C.

In an alternate preparation method, the nickel is first added to the calcium phosphate gel by adding an aqueous solution of a soluble nickel compound to the slurry of the calcium phosphate gel, with stirring, together with an alkaline solution of, for example, ammonium hydroxide, an alkali metal hydroxide or an alkali metal carbonate to maintain a pH of at least 7, preferably 7 to 9, in the resulting mixture. The nickel/calcium phosphate gel is then filtered, washed, refiltered and dried in air at about 105° C. The dried material is then impregnated with an aqueous solution of the promoter metal compound and redried at about 105° C.

The dry catalyst material can then be crushed or otherwise reduced to granules and used directly, or it can be pulverized to about 20–40 mesh size and the powdered product treated with a lubricant and pressed into the form of a pellet or granule of a size suitable for catalyst use. The catalyst material is calcined in the presence of an oxygen-containing gas or air at a temperature in the range of about 300°–650° C. for about 30 minutes to 10 hours or more. Prior to use, the calcined material is heated in a reducing atmosphere such as hydrogen at a temperature in the range of about 300°–650° C. for a period of about 30 minutes to 10 hours or longer. Alternatively, the dried catalyst material can be reduced, as above, without prior calcination.

Suitable nickel compounds for use in the catalyst preparation include nickel acetate, nickel nitrate, and nickel sulfate. Suitable barium compounds for use as promoter compounds providing a source of barium promoter include barium acetate, barium benzoate, barium butyrate, barium formate, barium nitrate, barium nitrite, barium propionate, and barium salicylate. Suitable uranium compounds for use as promoter compounds providing a source of uranium promoter include uranyl acetate, uranyl formate, and uranyl nitrate.

Although soluble halide compounds such as the calcium halides, nickel halides, barium halides and uranyl halides can be used to prepare the catalyst, halides are not normally used because of the difficulty of removing halide anions from the catalyst material during calcining and washing.

The hydrogenation reaction is carried out in the presence of excess hydrogen gas. The mole ratio of hydrogen to aromatic hydrocarbon charged to a fixed bed reactor can be, for example, 2–5 times the stoichiometrically required concentration.

The invention hydrogenation reaction can be carried out as a continuous process over a fixed catalyst bed or as a batch process in, for example, a stirred autoclave.

The pressures for the invention hydrogenation process can range from about atmospheric to 7 MPa or higher. The preferred pressure for the invention hydrogenation process is from about 800 kPa to about 3500 kPa.

The temperature for the invention process can range from about 65° to about 315° C. However, temperatures in the range of about 130° to 230° C. are preferred for benzene hydrogenation because of the incidence of ring opening by hydrogenolysis at temperatures above about 260° C. and because of the longer catalyst life at relatively low temperature. Particularly desirable conditions for benzene or toluene hydrogenation according to the invention process, because of the increased catalyst life which could be realized, include liquid-phase reaction at a temperature of about 150° C. and a pressure of about 1275 kPa.

The unsaturated hydrocarbon can be fed to the reaction zone at a rate of about 0.1 to 2 volumes per volume of catalyst per hour, preferably about 0.75–1. The total feed rate will generally be much larger, as the unsaturated hydrocarbon is usually diluted with unreactive hydrocarbons to control the temperature rise in the reaction zone during the exothermic hydrogenation reaction. Any of the conventional saturated hydrocarbon diluents can be used, but the preferred diluent is the product of saturating the feedstock, i.e., benzene is diluted with cyclohexane and toluene with methylcyclohexane. Feedstock to the hydrogenation process containing about 10 mole percent unsaturated hydrocarbon is usually suitable.

EXAMPLE I

This example illustrates the preparation of a catalyst suitable for use in the invention hydrogenation process. The catalyst, referred to as catalyst A in Example II below, was prepared by adding an aqueous solution of dipotassium hydrogen phosphate (1.0 mole) with vigorous stirring to an aqueous solution of calcium acetate (1.67 moles) to obtain a calcium phosphate gel having a Ca:P atomic ratio of 1.67. The gel was allowed to stand overnight and was recovered by filtration and was washed by slurrying in a 3500 mL portion of water 3 times, with filtering after each wash. The filter cake was additionally washed by pulling 10 liters of distilled water through it. About one quarter of the wet cake was reslurried in 1000 mL of distilled water, and to the stirred slurry was added 16 grams of barium nitrate dissolved in 300 mL of distilled water. The mixture was allowed to stand for 2 days with occasional stirring. Then to the well-stirred slurry was slowly added a mixture of 145 g nickel nitrate and 16 g barium nitrate dissolved in 600 mL of hot distilled water and 100 g potassium carbonate dissolved in 250 mL of distilled water. The resulting mixture was filtered to obtain a cake which was reslurried in about 3500 mL of distilled water and filtered. This operation was repeated and then about 3 liters of distilled water was pulled through the filter cake. The cake was dried overnight at 220° F., crushed to pass a 40-mesh screen and calcined in air at 800° F. for 3 hours. The cooled product was mixed with 3 weight percent polyethylene powder and pilled to ⅛-inch size at 100 psig. The pills were heated at about 800° F. in hydrogen for about 20 minutes to obtain the finished catalyst. The catalyst, as analyzed, contained 16.3 weight percent barium and 26.9 weight percent nickel based on the total weight of the catalyst. The surface area of the catalyst was about 80 square meters per gram, as determined by nitrogen absorption, the pore volume was about 0.2 mL per gram as determined by water absorption, and the apparent bulk density was 0.94 gram per mL.

EXAMPLE II

A set of runs was performed in which benzene was hydrogenated using three different catalysts. Catalyst A was prepared as described in Example I. Catalyst B was G-87 catalyst obtained from Girdler. It contains 40 weight percent nickel on a refractory oxide and is made especially for benzene hydrogenation. Catalyst C was R-28 catalyst obtained from the Davison Chemical Division of W. R. Grace Co. It was a fine particle size Raney nickel which had been activated by the vendor and stored under mineral oil, and was used without additional treatment. A use suggested by the vendor for this material is benzene hydrogenation.

Prior to their use, portions of catalysts A and B were crushed and sieved and −24 to +80 mesh fractions were collected. They were prereduced under flowing hydrogen at about 370° C.

Catalysts A, B and C were used separately in runs made as follows: A 300-mL stirred autoclave containing 100 mL of benzene was purged with nitrogen. The quantity of catalyst indicated in Table I was then added. The autoclave was heated to 70° C. and then pressurized with hydrogen to 2.17 MPa (300 psig). The time required for the pressure to fall to 1.14 MPa (150 psig) was measured. Consumption of that quantity of hydrogen was sufficient to convert slightly over two percent of the benzene to cyclohexane. The temperature rise accompanying this conversion was 2°–3° C. Conversion was limited to low values to permit comparison at nearly isothermal conditions. The results of the runs are summarized in Table I.

TABLE I

| Catalyst | Wt. (g) | $C_6H_6$ Conv. (%) | Time (hr.) | Rate[b] |
|---|---|---|---|---|
| A | 4.3 | 2.18 | 0.33 | 0.0173 |
| B | 4.4 | 2.47 | 0.75 | 0.0084 |
| C | 5 | —[a] | 1.0 | Negligible |

[a] At 149° C. this catalyst was very active, indicating that failure to hydrogenate at 70° C. was not caused by the presence of catalyst poison.
[b] Moles cyclohexane ÷ (hours × g catalyst)

A comparison of the runs shows that the nickel on calcium phosphate catalyst had high activity in the liquid-phase hydrogenation of benzene to cyclohexane. The invention process using catalyst A resulted in a rate nearly twice the rate of the hydrogenation using catalyst B and much faster than the rate using catalyst C. Catalyst C showed high activity at 149° C. but gave poor results at 70° C., the temperature at which catalysts A and B were run.

That which is claimed is:

1. A method for the hydrogenation of an unsaturated hydrocarbon comprising contacting the unsaturated hydrocarbon with hydrogen under suitable hydrogenation conditions in the presence of a catalyst comprising nickel on a calcium phosphate support, wherein an effective amount of said nickel is free of chemical combination with phosphorus.

2. The method of claim 1 in which the catalyst further comprises at least one of barium and uranium.

3. The method of claim 2 in which the unsaturated hydrocarbon is an aromatic hydrocarbon.

4. The method of claim 3 in which the aromatic hydrocarbon is selected from benzene and toluene and the hydrogenation conditions include a temperature in the range of about 130° to about 230° C. and a pressure in the range of about 800 kPa to about 3.5 MPa.

5. The method of claim 3 in which the hydrogenation is carried out in liquid phase.

6. The method of claim 1 in which nickel is present in the catalyst in an amount within the range of about 10 to about 50 weight percent based on the weight of the catalyst and the atomic ratio of calcium to phosphorus is within the range of about 1.4:1 to about 2.3:1.

7. The method of claim 6 in which the catalyst further comprises barium present in an amount within the range of about 1 to about 20 weight percent based on the weight of the total catalyst.

8. The method of claim 7 in which the nickel is present in an amount within the range of about 20 to about 40 weight percent, based on the weight of the catalyst.

9. The method of claim 6 in which the catalyst further comprises uranium present in an amount within the range of about 2 to about 40 weight percent, based on the weight of the catalyst.

10. The method of claim 9 in which the nickel is present in an amount within the range of about 20 to about 40 weight percent, based on the weight of the catalyst.

11. The method of claim 8 in which the unsaturated hydrocarbon is benzene and the hydrogenation is carried out in liquid phase.

12. The method of claim 2 in which the catalyst is prepared by a method comprising admixing an aqueous solution of a calcium salt and an aqueous solution of a phosphate compound to form a calcium phosphate gel having a Ca:P atomic ratio in the range of about 1.4:1 to about 2.3:1, introducing into the calcium phosphate gel an aqueous nickel solution and at least one aqueous solution of at least one of barium and uranium, recovering the thus-treated gel, drying the recovered gel, heating the dried gel in the presence of oxygen at a temperature in the range of about 300° to about 650° C. for at least 0.5 hour, and then heating the dried gel in a reducing atmosphere at a temperature in the range of about 350° to about 650° C. for at least about 0.5 hour.

* * * * *